United States Patent [19]

Swanson et al.

[11] Patent Number: 5,392,764
[45] Date of Patent: Feb. 28, 1995

[54] GYNECOLOGICAL SPECULUM

[76] Inventors: Larry S. Swanson, 2166 Sandy Shore Dr. SE., Kentwood, Mich. 49508; Lawrence J. Burns, 1556 Pontiac Rd., SE, Grand Rapids, Mich. 49506

[21] Appl. No.: 79,367

[22] Filed: Jun. 18, 1993

[51] Int. Cl.$^6$ .................. A61B 1/30; A61M 29/00
[52] U.S. Cl. ................................ 128/3; 128/9; 606/197
[58] Field of Search ............ 128/3, 5, 9, 20, 17, 128/18, 10, 11, 12, 13, 15, 16; 606/197

[56] References Cited

U.S. PATENT DOCUMENTS

| | | | |
|---|---|---|---|
| 218,055 | 7/1879 | Nitze | 128/11 |
| 267,906 | 11/1882 | Law | 128/5 |
| 424,140 | 3/1890 | Shuford | 128/17 |
| 949,236 | 2/1910 | Kaplan et al. | 128/18 |
| 1,629,119 | 3/1927 | Reitz | 606/197 |
| 2,483,233 | 9/1949 | Price et al. | 128/17 |
| 3,132,645 | 5/1964 | Gasper | 128/3 |
| 3,949,740 | 4/1976 | Twentier | 128/9 |
| 4,206,750 | 6/1980 | Kaivola | |
| 4,712,536 | 12/1987 | Hawks | 128/3 |
| 4,957,486 | 9/1990 | Davis | 606/197 X |
| 5,135,526 | 8/1992 | Zinnanti et al. | 128/3 X |
| 5,183,464 | 2/1993 | Dubrul et al. | 128/3 |

FOREIGN PATENT DOCUMENTS 9307800 4/1993 WIPO .................. 128/17

OTHER PUBLICATIONS

Graham-Field Catalog, p. 200, Item #90-3546A.

*Primary Examiner*—Richard J. Apley
*Assistant Examiner*—Donna L. Maraglio
*Attorney, Agent, or Firm*—Brooks & Kushman

[57] ABSTRACT

A gynecological speculum for insertion through a vaginal orifice into a vaginal cavity for performing medical examinations or surgical procedures. The gynecological speculum comprises a tubular section having an open insertion end and an open user end and an interior surface and an exterior surface. A projection is provided on the exterior surface to engage the vaginal orifice and retain the speculum within the vaginal cavity after insertion. In a preferred embodiment, the tubular section tapers outwardly from the open insertion end to the open user end. In an alternative embodiment, a vacuum tube is connected to the tubular section for a evacuating the vaginal cavity by suction during medical proceedings.

8 Claims, 2 Drawing Sheets

GYNECOLOGICAL SPECULUM

TECHNICAL FIELD

The present invention relates to an improved gynecological speculum for examinations and surgical procedures.

BACKGROUND ART

In performing gynecological endoscopic examinations or surgical procedures, it is desirable to dilate the vaginal orifice in order to examine or operate on structures within the vaginal cavity such as the cervix. In order to make such examinations, or perform such surgical procedures, a duck-billed speculum is conventionally employed.

The conventional duck-billed speculum comprises two members; an upper member having a downward facing duck-billed portion connected to a handle portion at an obtuse angle, and a lower member having an upward facing duck-billed portion connected to a handle portion at an acute angle. The two members are pivotally attached to each other at the points of angulation such that the duck-billed portions separate from each other when the handle portions are urged toward each other. The handle portion of the upper member has an opening which establishes a line of sight into the space formed by the opposing duck-billed portions of the upper and lower members. In some cases, conventional duck-billed specula are provided with a locking mechanism to lock the duck-billed portions in desired positions of separation for the duration of the examination or surgical procedure.

Such conventional duck-billed specula may also be provided with a vacuum tube, built into the duck-bill portion of the upper member, which may be connected to a vacuum apparatus for evacuating the vaginal cavity, by suction, of gases or vapors during medical proceedings. In certain types of surgical procedures, such as those using laser or leep technology, the Occupational Safety and Health Act requires the use of vacuum tubes because the resulting gases or vapors can be toxic.

These conventional duck-bill specula are used by inserting the duck-billed portion through the vaginal orifice in a closed position. Once inserted, the user may urge the handle portions toward each other to dilate the vaginal orifice as desired. The vaginal cavity is then exposed and the user may perform desired medical procedures through the opening in the handle portion of the upper member. An example of a conventional duck-billed speculum apparatus is disclosed in U.S. Pat. No. 4,206,750 which issued on Jun. 10, 1980 to Kaivola.

The disadvantages inherent in the conventional duck-billed specula are several. Because the duck-bills must be urged apart in order to dilate the vaginal orifice, body tissue is not only exposed on each side of the duck-bills, but may also protrude into the resulting gap between the duck-bills. This results in two disadvantages. First, during surgical procedures involving laser, leep, scalpels, or other surgical cutting apparatus, the surrounding body passage tissue is subject to being accidentally cut or burned. Secondly, tissue protruding into the gap between the duck-bills is subject to being pinched within the duck-bill mechanism. Such pinching will not only cause the patient pain or injury, it may also cause the patient to tense up, thereby interfering with the medical procedure being performed.

Another disadvantage is that due to the mechanical and configuration requirements of duck-billed specula, and the protrusion of surrounding tissue into the gap formed between the duck-bills, the viewing aperture formed between the duck-bills when dilated is relatively small. Likewise, the work space between the duck-bills is also relatively small. As a result, the line of sight and space provided for examinations and surgical procedures is limited.

Yet another disadvantage is the fact that conventional duck-billed specula employ a mechanical hinge which is not only subject to breakage, especially in the case of plastic specula, but is also more expensive to manufacture and assemble. Furthermore, the mechanical hinge is disadvantageous because it can pinch or catch the flesh or hair of the patient.

Another type of conventional speculum comprises a cylindrical tube having an outwardly tapering user end such as the one sold by Graham-Field and illustrated in FIG. 7. The disadvantages inherent in this design are as follows.

First, there is nothing to prevent such a speculum from sliding out of the vaginal cavity in which it is being used. Instead, the user must hold this speculum in place or continually push it back into position. Second, there is no provision for a vacuum tube connection. An operator using such a speculum must insert and support a vacuum tube through the limited cylindrical opening available. Third, the cylindrical configuration of this speculum limits the space available at the user end for performing medical procedures.

Accordingly, there remains a need for a simple gynecological speculum which offers the medical user the maximum aperture available in which to examine and operate on a patient, which is retained within the vaginal cavity into which it has been inserted, and which also provides for evacuation of the vaginal cavity by suction during medical proceedings.

SUMMARY OF THE INVENTION

An object of the present invention is to provide a new and improved gynecological speculum for medical examinations and surgical procedures.

In carrying out the above objects, and other objects and features of the present invention, a new and improved gynecological speculum is provided. The gynecological speculum comprises a tubular section having an interior surface and an exterior surface and a projection on the exterior surface to engage the vaginal orifice and retain the speculum within the vaginal cavity after insertion. The tubular section also has an open insertion end and an open user end and preferably tapers outwardly from the open insertion end to the open user end.

In an alternative embodiment of this invention, a vacuum tube is also provided and connected to the tubular section for evacuating the vaginal cavity by suction during medical proceedings.

The advantages accruing to the present invention are numerous. For example, use of this speculum is simple and does not require the user to operate a mechanism. The speculum may be simply lubricated and slid into the desired position through the vaginal orifice. An additional advantage resulting from the lack of a mechanism is the lesser likelihood of breakage.

Another advantage is that the projection on the exterior surface engages the vaginal orifice and retains the speculum within the vaginal cavity after insertion without the need to hold the speculum in position or to lock any type of mechanical device.

Yet another advantage is that the user is given a better line of sight through the open user end of the speculum and more space to operate within the entire length of the speculum during medical procedures.

A further advantage is the 360° of protection provided to prevent surrounding tissue from being accidentally nicked or burned during surgical procedures.

An advantage provided by the alternative embodiment including a vacuum tube is that the vaginal cavity may be easily evacuated of gases or vapors during medical proceedings by attaching a suction device to the vacuum tube. It is not necessary for the user to insert and support a vacuum tube within the vaginal cavity during use of this alternative embodiment.

These objects, and other objects, features, and advantages of the present invention, will be readily appreciated by one of ordinary skill in the art from the following detailed description of the best mode for carrying out the invention when taken in connection with the accompanying drawings.

BEST MODE FOR CARRYING OUT THE INVENTION

Figure 1:
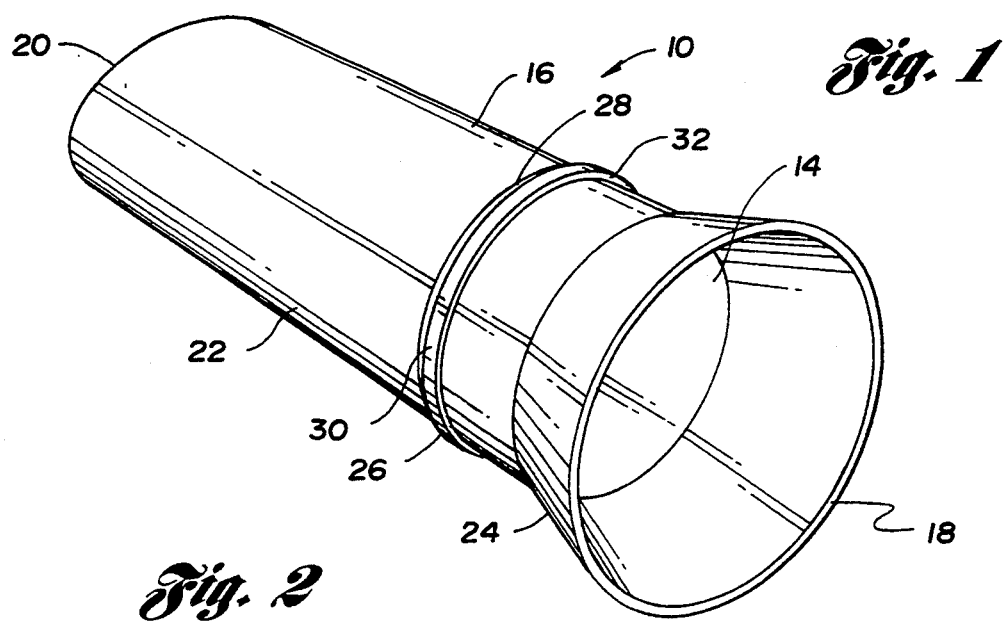
FIG. 1 is a perspective view of one embodiment of the improved gynecological speculum of the present invention.
Figure 2:
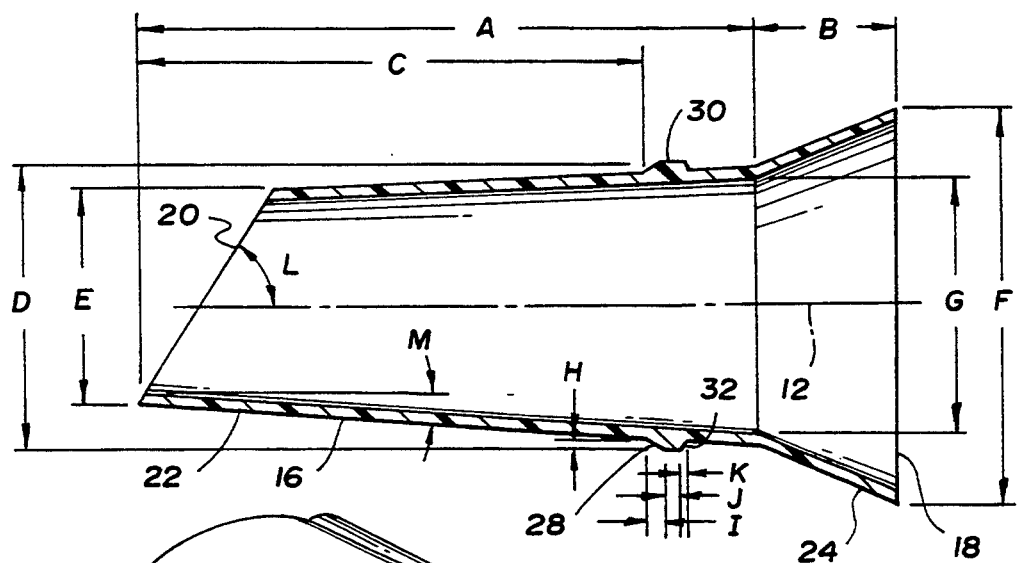
FIG. 2 is a cut away side view of the one embodiment of the improved gynecological speculum.
Figure 3:
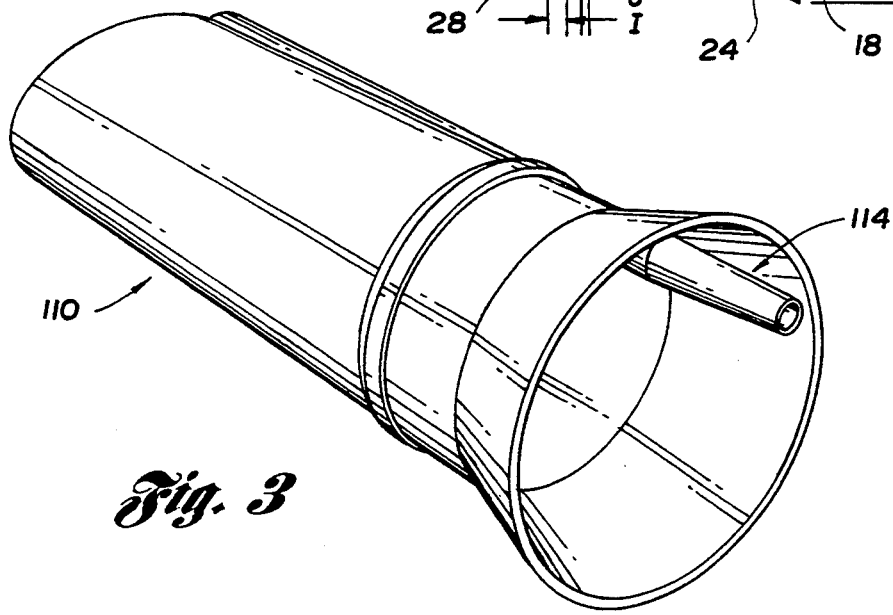
FIG. 3 is a perspective view of a second embodiment of the improved gynecological speculum of the present invention which includes a vacuum tube.
Figure 4:
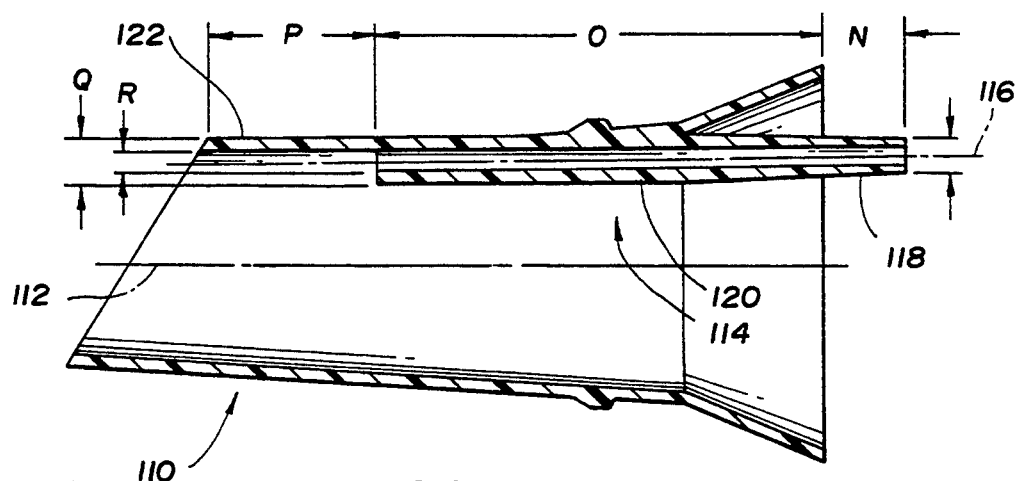
FIG. 4 is a cut away side view of the second embodiment of the improved gynecological speculum.
Figure 5:
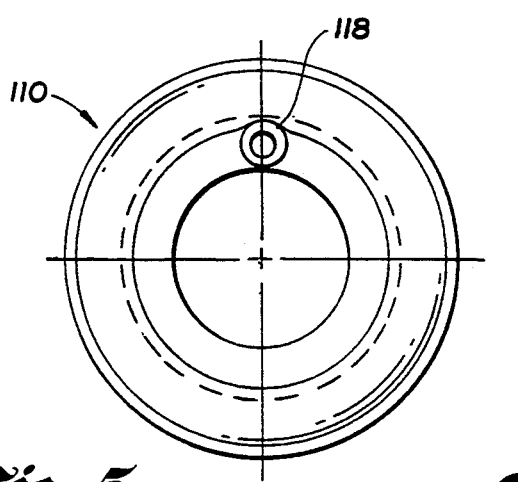
FIG. 5 is an elevational view of the open user end of the second embodiment of the improved gynecological speculum.
Figure 6:
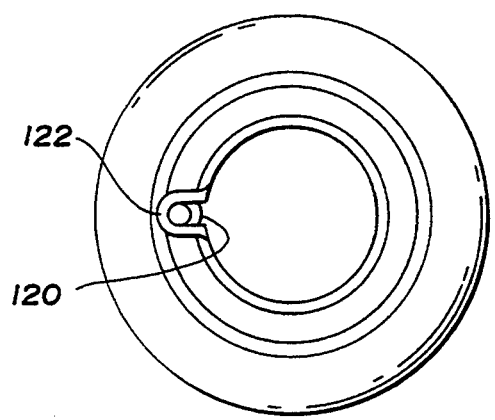
FIG. 6 is an elevational view of the open insertion end of the second embodiment of the improved gynecological speculum.
Figure 7:
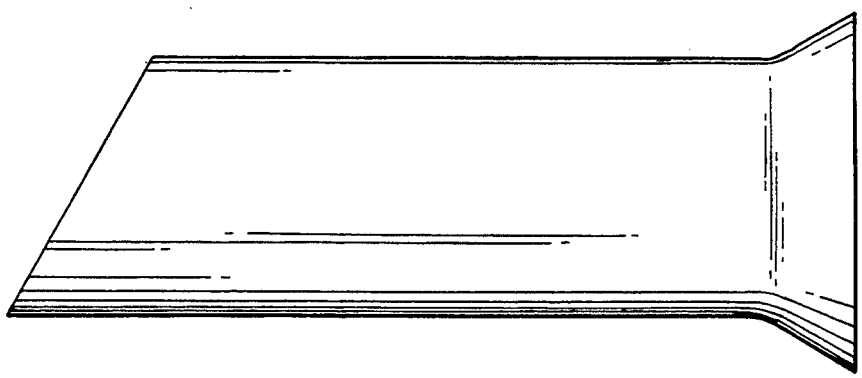
FIG. 7 is a perspective view of a prior art gynecological speculum.

As shown in FIGS. 1 and 2, one embodiment of the improved gynecological speculum of the present invention comprises a tubular section 10 having a center axis 12. While the tubular section 10 preferably has a circular cross-section it could also have an oval or other appropriate cross-section. The tubular section 10 has an interior surface 14 and an exterior surface 16. The tubular section 10 also has a open user end 18 and an open insertion end 20. In the preferred embodiment shown, the tubular section 10 comprises two coaxially aligned and integral segments, a first frusto-conical segment 22 and a second frusto-conical segment 24.

The first frusto-conical segment 22 defines a projection which in the preferred embodiment shown constitutes an annular lip 26 which engages the vaginal orifice during use thereby retaining the speculum within the vaginal cavity. The projection may also comprise an annular groove or any other configuration which would likewise serve the purpose of engaging the vaginal orifice. The annular lip 26 preferably has an inclined front surface 28, a flat top surface 30 and an inclined rear surface 32. The inclined front surface 28 serves to ease insertion of the annular lip 26 through the vaginal orifice thereby minimizing discomfort to the patient. The inclined rear surface 32 likewise serves the same purpose when the speculum is removed from the vaginal orifice. However, the inclined rear surface 32 has a steeper surface to engage the vaginal orifice and to retain the first frusto-conical segment 22 within the vaginal cavity during medical procedures.

The second frusto-conical segment 24 protects the surrounding exterior tissue from being accidentally nicked or burned during surgical procedures. In the event the vaginal structure of a patient is atypical, the second frusto-conical segment 24 may also serve to prevent the open user end 18 from being pushed completely through and into the vaginal orifice during use.

For gynecological examinations and surgical procedures, the following preferred dimensional parameters have been developed to minimize discomfort to the majority of patients while maximizing the line of sight and space available to examine and operate on the majority of patients.

| Parameter Symbol | Preferred Parameter |
| --- | --- |
| A | 11 cm. |
| B | 2.5 cm. |
| C | 9 cm. |
| D | 5 cm. |
| E | 4.1 cm. |
| F | 7 cm. |
| G | 4.5 cm. |
| H | 0.225 cm. |
| I | 0.4 cm. |
| J | 0.2 cm. |
| K | 0.2 cm. |
| L | 60° |
| M | 4° |

Regarding the length A of the first frusto-conical section 22, and the dimension C from the open insertion end 20 to the annular lip 26, it has been determined that the lengths of 11 cm. and 9 cm. respectively are preferable. Upon insertion of the speculum for examinations and surgical procedures, these dimensions will properly position the open insertion end 20 relative to the cervix in most patients. Because the cervix is normally oriented at an angle to the vaginal passageway, the open insertion end is preferably formed at an angle L which has been determined to be preferably 60°. The angled open insertion end 20 also serves to facilitate insertion of the speculum through the vaginal orifice.

Different outside diameters D of the annular lip 26 have been tested. As a result, it has been determined that the preferred outside diameter D which minimizes discomfort to most patients while maximizing the inner dimension of the speculum is 5 cm. As noted, the inclined front surface 28 and rear surface 32 of the annular lip 26 should be inclined to ease entry of the speculum into and out of the vaginal orifice. The preferred parameters indicated for H, I, J and K provide an inclined front surface 28 having a slope of approximately 15° relative to the center axis 12 and an inclined rear surface 32 having a slope of approximately 45° relative to the center axis 12.

To maximize the opening at the open insertion end 20 and the space within the tubular section 10, while minimizing discomfort to the typical patient, it has been determined that the first frusto-conical segment 22, having the preferred opening dimension E of 4.1 cm., preferably has a taper angle M of 4° relative to the center axis 12 of the tubular section 10.

An alternative embodiment of the invention, as shown in FIGS. 3, 4, 5 and 6, is identical to the embodiment illustrated in FIGS. 1 and 2 except that the tubular section 110 having a center axis 112 also defines a vacuum tube 114 having a center axis 116. The vacuum tube 114 has a nipple end 118, a cylindrical portion 120 and a partial cylindrical portion 122. The nipple end 118 facilitates the connection of a suction device (not shown) to the vacuum tube 114. The partial cylindrical portion 122 provides a collection area at the top of the tubular section 110 for gases and vapors which are to be evacuated by suction via the vacuum tube 114. For ease of manufacture, the center axis 116 of the vacuum tube 114 is parallel to the center axis 112 of the tubular section 110.

All of the preferred dimensions and angles provided with regard to the first embodiment are also applicable to this alternative embodiment with the exception of those dimensions for the vacuum tube which are provided in the following table.

| Dimension Parameter Symbol | Preferred Dimension |
|---|---|
| N | 1.5 cm. |
| O | 8.0 cm. |
| P | 3.0 cm. |
| Q | 0.8 cm. |
| R | 0.4 cm. |
| S | 0.6 cm. |

The improved gynecological speculum of the present invention may be manufactured from any material suitable for medical purposes. If it is desired to supply the speculum as a throwaway item, the speculum may be formed from Medical Grade 6 Polycarbonate having a preferable wall thickness of 0.2 cm. In the event such a material is used, the wall thickness may narrow at the tapered end of the nipple end 118 where the preferred wall thickness will be 0.1 cm.

If the speculum is to be sanitized and reused, or if it is to be subjected to surgical techniques which could lead to melting of the Polycarbonate material, it may be manufactured from stainless steel or glass. In any event, the speculum must be manufactured without any sharp edges.

It is understood, of course, that while the forms of the invention shown and described constitute preferred embodiments, they are not intended to illustrate all possible forms of the invention. It will also be understood that the words used are words of description rather than limitation, and that various changes may be made without departing from the spirit and scope of the invention disclosed.

What is claimed is:

1. A gynecological speculum for insertion through a vaginal orifice into a vaginal cavity for medical purposes, the gynecological speculum comprising:
    an imperforate tubular section having a tube axis and coaxially aligned and integral segments, the segments comprising a first frusto-conical segment and a second frusto-conical segment;
    the first frusto-conical segment having a maximum outside diameter end and a substantially planar open insertion end inclined at an angle other than perpendicular relative to the tube axis to facilitate insertion of the open insertion end, without the need for extra equipment, through the vaginal orifice and into the vaginal cavity to isolate the cervix, and the second frusto-conical section having a minimum outside diameter end equal in diameter to and adjoining the maximum outside diameter end of the first frusto-conical segment; and
    the first frusto-conical segment defining an annular lip near the maximum outside diameter end to engage the vaginal orifice and retain the gynecological speculum within the vaginal cavity after insertion of the first frusto-conical section through the vaginal orifice.

2. The gynecological speculum of claim 1 wherein the open insertion end is inclined at an angle of approximately 60° relative to the tube axis.

3. The gynecological speculum of claim 1 wherein the outside diameter of the annular lip is approximately five centimeters.

4. The gynecological speculum of claim 1 wherein:
    the first frusto-conical segment has a first axis, defines the open insertion end formed at an angle of approximately 60° relative to the first axis, has a length of approximately 11 centimeters, has a maximum first outside diameter opposite the open insertion end of approximately 4.9 centimeters, has a taper of approximately 4° relative to the first axis, and the annular lip has a maximum outside lip diameter of approximately 5 centimeters; and
    the second frusto-conical segment has a second axis, defines the open user end, has a length of approximately 2.5 centimeters, and has a taper in the range of 23° relative to the second axis.

5. A gynecological speculum for insertion into a vaginal orifice for medical purposes, the gynecological speculum comprising:
    an imperforate tubular section having a tube axis and coaxially aligned and integral segments, the segments comprising a first frusto-conical segment and a second frusto-conical segment;
    the first frusto-conical segment having a maximum outside diameter end and a substantially planar open insertion end inclined at an angle other than perpendicular relative to the tube axis to facilitate insertion of the open insertion end, without the need for extra equipment, through the vaginal orifice and into the vaginal cavity to isolate the cervix, and the second frusto-conical section having a minimum outside diameter end equal in diameter to and adjoining the maximum outside diameter end of the first frusto-conical segment;
    the first frusto-conical segment defining an annular lip near the maximum outside diameter end to engage the vaginal orifice and retain the gynecological speculum within the vaginal cavity after insertion of the first frusto-conical section through the body orifice; and
    a vacuum tube connected to the first frusto-conical segment for evacuating the body cavity by suction during medical proceedings.

6. The gynecological speculum of claim 5 wherein the open insertion end is inclined at an angle of approximately 60° relative to the tube axis.

7. The gynecological speculum of claim 5 wherein the outside diameter of the annular lip is approximately five centimeters.

8. The gynecological speculum of claim 5 wherein:

the first frusto-conical segment has a first axis, defines the open insertion end formed at an angle of approximately 60° relative to the first axis, has a length of approximately 11 centimeters, has a maximum first outside diameter opposite the open insertion end of approximately 4.9 centimeters, has a taper of approximately 4° relative to the first axis, and the annular lip has a maximum outside lip diameter of approximately 5 centimeters; and the second frusto-conical segment has a second axis, defines the open user end, has a length of approximately 2.5 centimeters, and has a taper in the range of 23° relative to the second axis.

* * * * *